(12) United States Patent
Shiao et al.

(10) Patent No.: US 6,299,442 B1
(45) Date of Patent: Oct. 9, 2001

(54) FIELD CALABRATABLE ARTICULATOR

(75) Inventors: John Shiao, Tainan (TW); Jesse Chen, Lynnwood, WA (US); Allen Steinbock, Louisville, KY (US)

(73) Assignee: Whip Mix Corporation, Louisville, KY (US)

( * ) Notice: Subject to any disclaimer, the term of this patent is extended or adjusted under 35 U.S.C. 154(b) by 0 days.

(21) Appl. No.: 09/500,296

(22) Filed: Feb. 8, 2000

Related U.S. Application Data
(60) Provisional application No. 60/120,054, filed on Feb. 15, 1999.

(51) Int. Cl.[7] .................................................. A61C 11/00
(52) U.S. Cl. ................................................................ 433/64
(58) Field of Search ................................. 433/54, 57, 58, 433/62, 64, 196

(56) References Cited

U.S. PATENT DOCUMENTS

| | | |
|---|---|---|
| 547,195 | 10/1895 | Antes . |
| 582,731 | 5/1897 | Fourt . |
| 659,871 | 10/1900 | Lewis . |
| 1,160,114 | 11/1915 | Snow . |
| 2,119,896 | 6/1938 | Van Dorn et al. . |
| 2,765,533 | 10/1956 | McMorris . |
| 2,824,371 | 2/1958 | Granger . |
| 3,052,030 | 9/1962 | Spence . |
| 3,224,096 | 12/1965 | Stuart . |
| 3,359,639 | * 12/1967 | Guichet ................................... 433/64 |
| 4,024,640 | 5/1977 | Guichet . |
| 4,096,632 | 6/1978 | Perry . |
| 4,128,942 | 12/1978 | Schleich . |
| 4,242,087 | 12/1980 | Lee . |
| 4,245,987 | 1/1981 | Bertoldi . |
| 4,352,662 | 10/1982 | Lee . |
| 4,439,150 | 3/1984 | Edwardson . |
| 4,445,855 | 5/1984 | Hobo et al. . |
| 4,496,319 | 1/1985 | Steinbock . |
| 4,556,387 | 12/1985 | Lee . |
| 4,687,442 | 8/1987 | Wong . |
| 4,721,463 | 1/1988 | Lee . |
| 4,764,113 | 8/1988 | Hiranuma . |
| 4,797,097 | * 1/1989 | Cohn ....................................... 433/64 |
| 4,865,544 | 9/1989 | Scruggs . |
| 5,009,594 | 4/1991 | West . |
| 5,338,193 | 8/1994 | Mack . |
| 5,431,564 | 7/1995 | Guichet . |

* cited by examiner

*Primary Examiner*—Todd E. Manahan
(74) *Attorney, Agent, or Firm*—Camoriano & Associates; Theresa Fritz Camoriano (57) ABSTRACT

An articulator that can be recalibrated easily in the field. The articulator has left and right condyle elements that resemble barbells, with an inner sphere, an outer sphere, and a shaft connecting the inner and outer spheres together. In the preferred embodiment, the outer spheres are releasably fixed to the lower frame member by clamping members, and the inner spheres are pivotably mounted to the upper frame member. To calibrate the articulator, the clamping members are loosened, an alignment fixture is installed to ensure that the articulator is in proper alignment, and then the clamping members are tightened into position, fixing the outer spheres in the properly-aligned position.

13 Claims, 8 Drawing Sheets

FIELD CALABRATABLE ARTICULATOR

This application claims priority from U.S. Provisional application Ser. No. 60/120,054, filed Feb. 15, 1999.

BACKGROUND OF THE INVENTION

The present invention relates to dental articulators, and, in particular, to a dental articulator which can be re-calibrated in the field.

Many different types of articulators are known in the art. They are used by dentists and dental laboratories to make dental prostheses on upper and lower casts of the patient's teeth that are in proper alignment, to make sure they will fit properly in the patient's mouth when they are in place. The dentist takes impressions of the patient's teeth and pours molds of the upper and lower arches using the impressions, and amounts the arches into the dentist's articulator, taking care to be sure the arches remain properly aligned. The dentist then sends those mounted arches to a dental laboratory to have the dental prosthesis, such as a bridge or set of false teeth made, and the dental laboratory uses the same type of articulator to be sure the prosthesis it makes will fit properly in the patient's mouth.

These articulators are carefully calibrated in the factory to be sure the castings will fit the same for every dentist and lab using the same type of articulator. If the articulator is dropped on the floor or otherwise jarred so as to put it out of alignment, the dentist or lab will send it back to the factory for recalibration. This means that there is a lag time during which the dentist or lab does not have the use of its articulator, and it means that there will be an expense involved in recalibrating the articulator. Some manufacturers of articulators have made products that can be recalibrated in the field, but they are either very difficult to use or do not have enough degrees of adjustment to ensure that they can be brought back into proper alignment.

SUMMARY OF THE INVENTION

The purpose of the present invention is to provide an articulator that can be recalibrated by the dentist or lab quickly, accurately, and easily, without requiring the articulator to be returned to the factory.

The present invention provides an articulator in which the parts involved in pivoting the articulator include two condyle elements, each shaped like a dumbbell having two spherical ends connected together by a shaft. In the preferred embodiment, each inner spherical element mounts to the respective receptacles on the upper frame of the articulator, and each outer spherical element is fixed by a clamp onto the lower frame of the articulator. To recalibrate the articulator, the dentist or lab technician simply loosens the clamp screws on the clamp holding the left and right outer spherical elements, secures lockout levers on the upper frame of the articulator, mounts a calibration device on the articulator to put the upper and lower frame members into proper alignment, and then re-tightens the clamp screws. Due to the shape and mounting arrangement of the condyle elements, the condyle elements can be shifted relative to the lower frame member in any direction along the outer spheres in order to put the articulator into alignment, and the alignment can all be done with one simple adjustment that is very accurate and easy to do. The clamp screws preferably have an unusually-shaped head requiring a special tool that is kept in a secure place, so that casual visitors to the dental office or dental lab will not be able to attempt recalibration just by using a regular screwdriver.

While the embodiment of the invention shown herein is used on a simple articulator, without adjustments, it will be clear to those skilled in the art that it can also be used on a much more complicated articulator having various adjustments.

DESCRIPTION OF THE PREFERRED EMBODIMENTS

Figure 1:
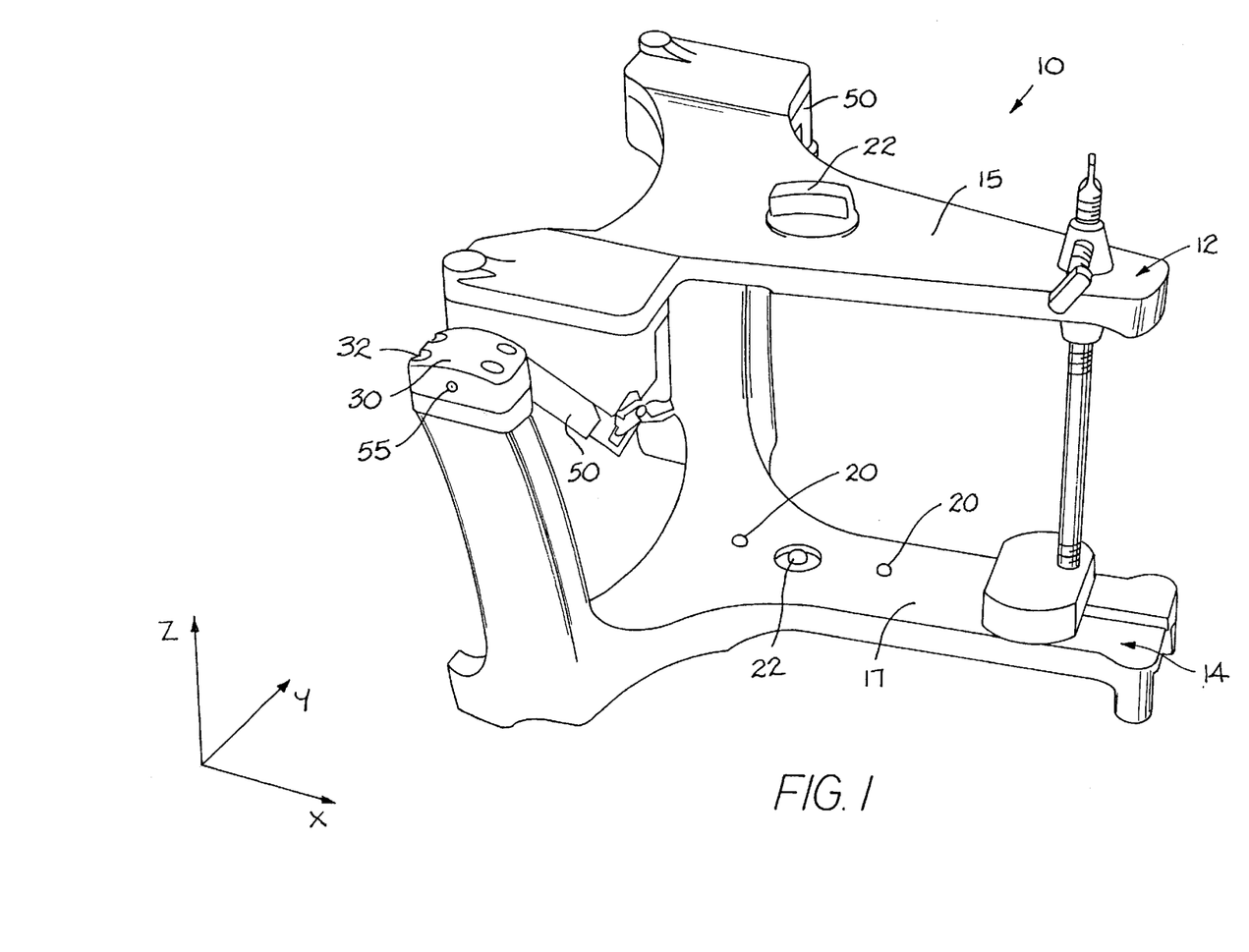
FIG. 1 is a perspective view of an articulator made in accordance with the present invention.
Figure 2:
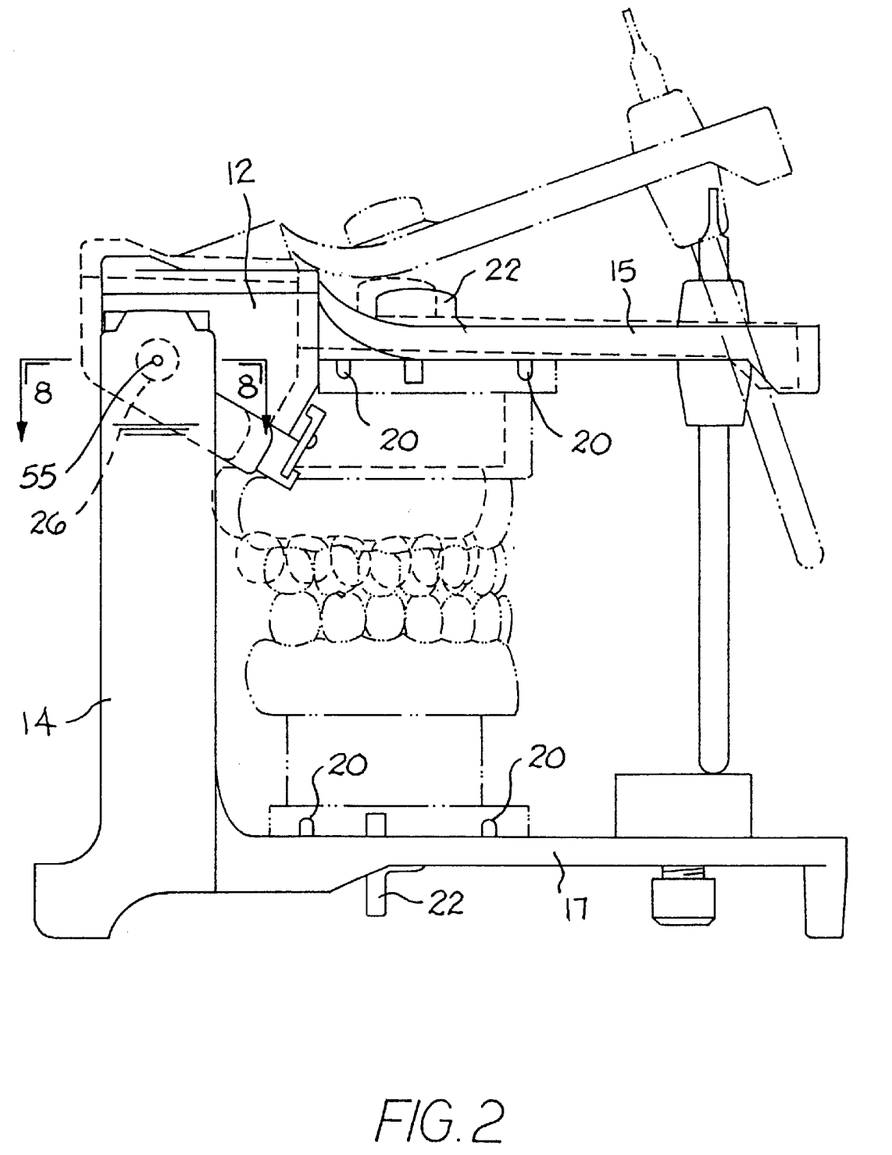
FIG. 2 is a side view of the articulator of FIG. 1, with a set of dental prostheses mounted to the articulator and showing in phantom how the upper frame member can be displaced laterally and can be pivoted relative to the lower frame member.

Referring to FIGS. 1–14, the articulator 10 includes two main pieces—an upper frame member 12 and a lower frame member 14, which pivot relative to each other through left and right condyle elements 16, 18, which are intended to mimic a person's jaw hinge. Each frame member 12, 14 has a respective forwardly-projecting arm 15, 17, each arm including its respective pair of alignment bumps 20 and its respective threaded connector 22, located between the alignment bumps 20. A mounting plate can be mounted on the alignment bumps and secured using the threaded connector 22. The dental arch is then positioned properly and attached to the mounting plate using a fast-set dental plaster as shown in FIG. 2.

Figure 7:
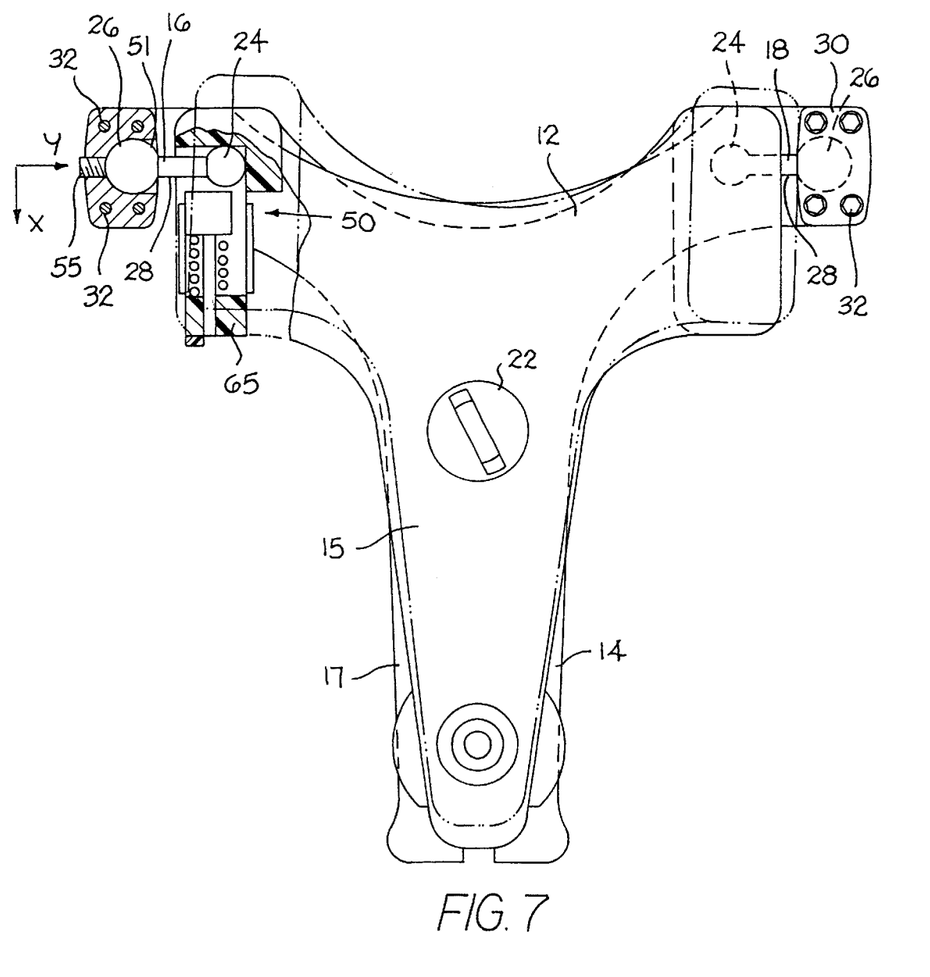
FIG. 7 is a top view, partially in section, of the articulator of FIG. 1 showing in phantom a lateral displacement of the upper frame member relative to the lower frame member of the articulator.
Figures 7A, 7B:
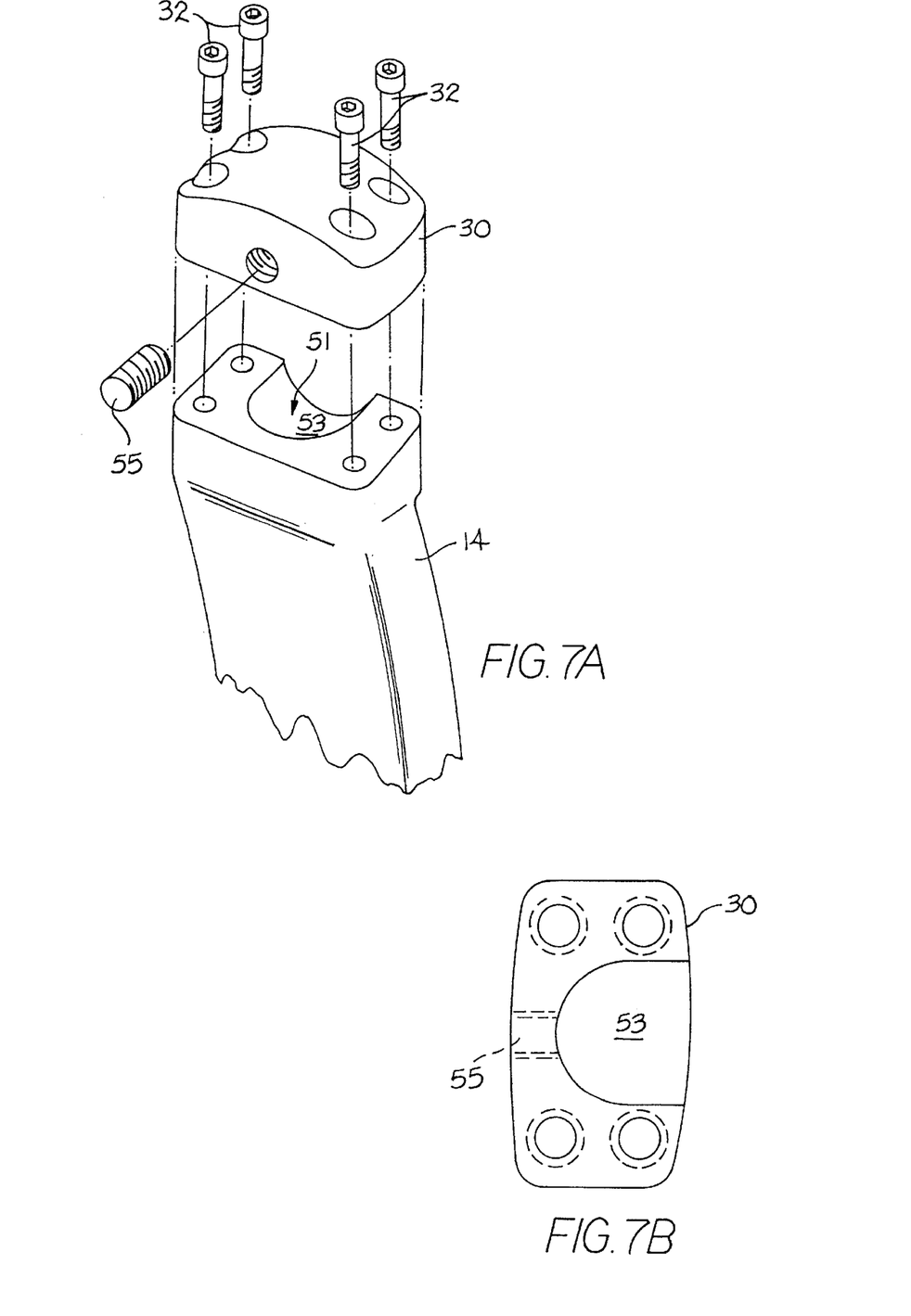
FIG. 7A is a broken-away, exploded perspective view of the left side of the lower frame member, showing the clamping mechanism.
FIG. 7B is a view of the underside of the clamping mechanism of FIG. 7A.
Figure 8:
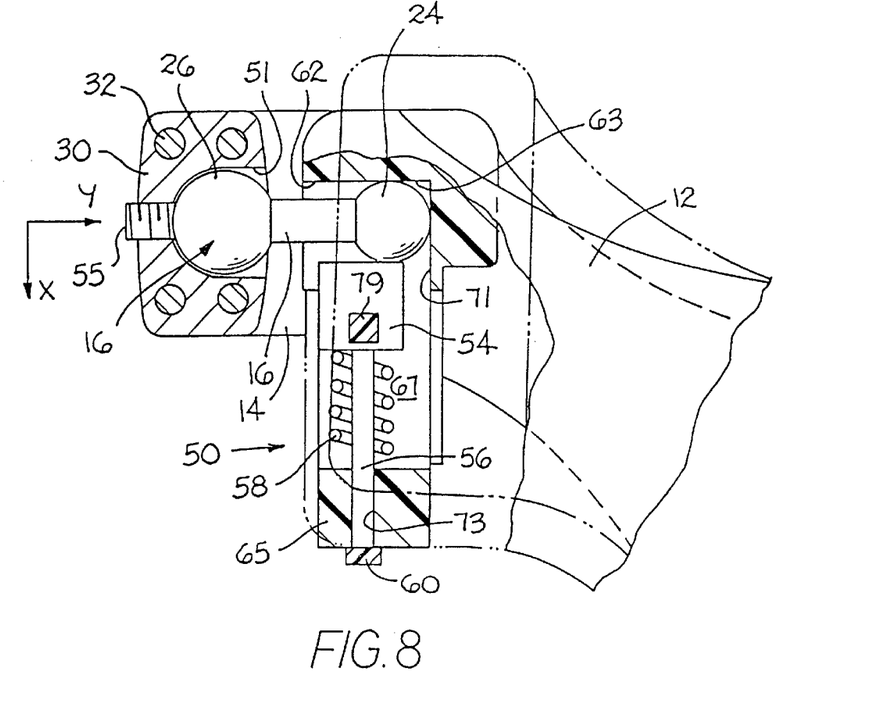
FIG. 8 is an enlarged, broken-away view taken along the section 8—8 of FIG. 2, which is the same view as the left portion of FIG. 7.
Figure 9:
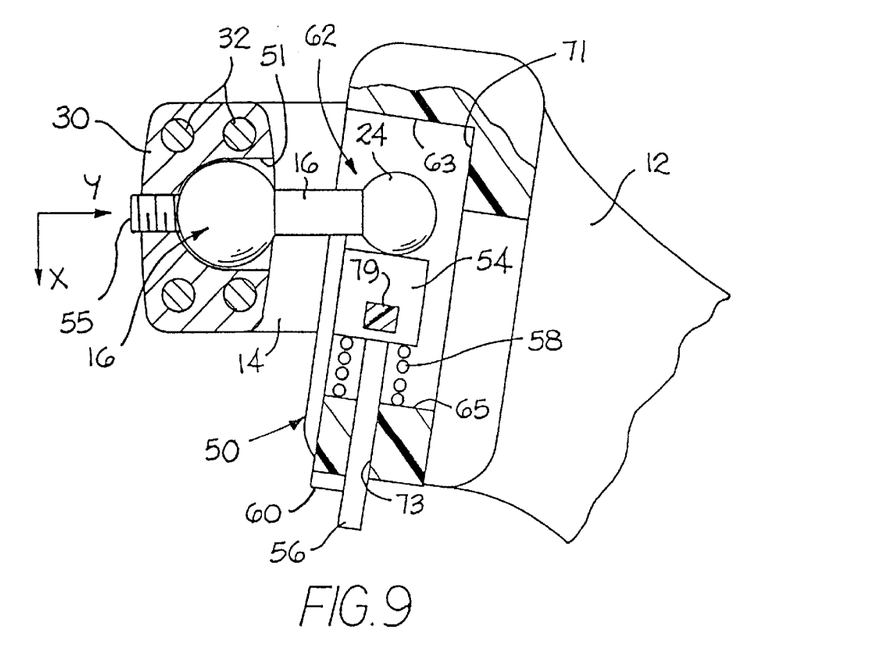
FIG. 9 is the same view as FIG. 8 except it shows the relative position of the components when the upper frame member is in the phantom position of FIG. 7.
Figure 10:
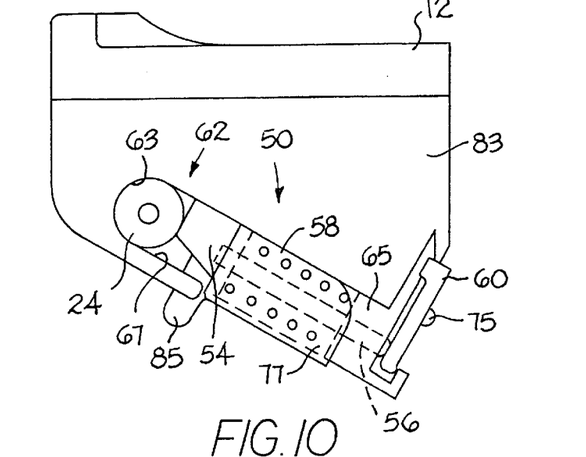
FIG. 10 is a side view, partially in section, of the condyle element and its housing in the upper frame member when in the bold position of FIGS. 7 and 8.
Figures 11, 12, 13, 14:
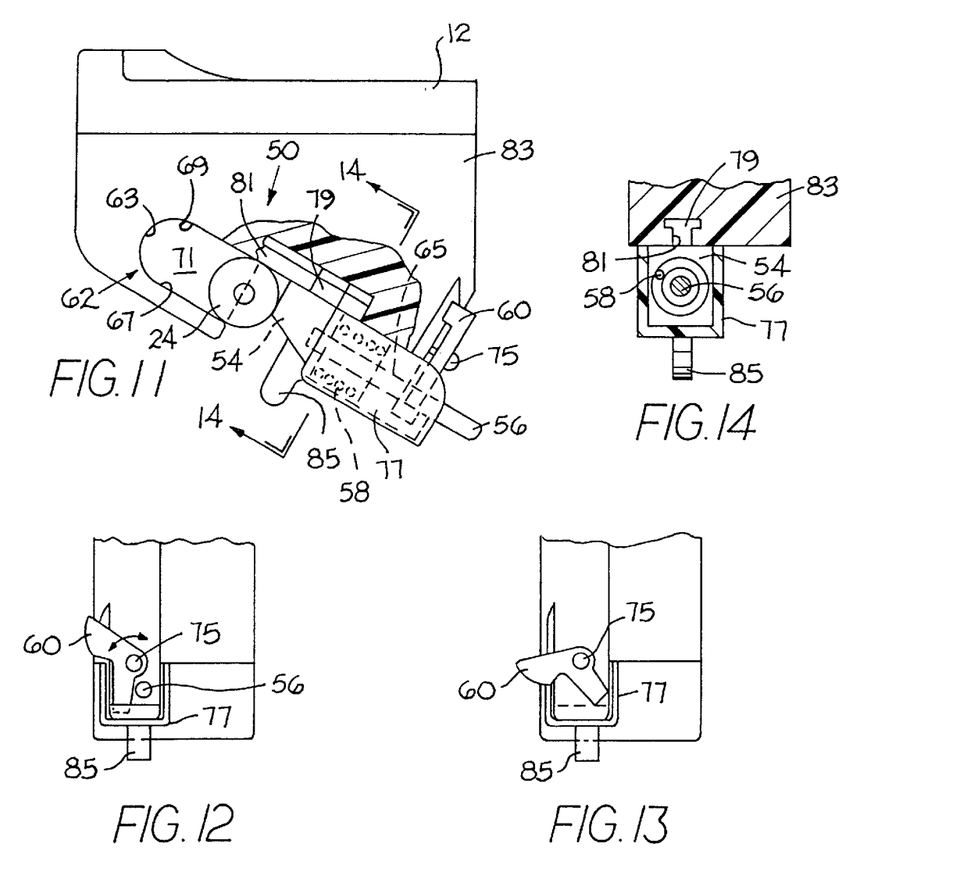
FIG. 11 is a side view, partially in section, of the condyle element and its housing in the upper frame member when in the phantom position of FIGS. 7 and 8.
FIG. 12 is a broken away detailed front view of the housing of FIG. 10, with the lockout lever mechanism open to allow movement in addition to pure rotation (movement such as depicted in FIGS. 2 and 7) of the upper frame member relative to the lower frame member.
FIG. 13 is a broken away detailed front view of the housing of FIG. 10 with the lockout lever mechanism closed so as to restrict movement to only pure rotation of the upper frame member relative to the lower frame member.
FIG. 14 is a view along the section 14—14 of FIG. 11.

As shown in FIG. 7, each condyle member 16, 18 is shaped somewhat like a dumbbell, with a smaller diameter inner sphere 24 and a larger diameter outer sphere 26 connected together by a shaft 28, which preferably is aligned with the centers of both spheres 24, 26. The left and right inner spheres 24 are received by left and right receptacles 50 in the upper frame member 12, as will be disclosed in more detail later, and the upper frame member 12 pivots relative to those inner spheres 24 when the upper and lower frame members pivot relative to each other, generally around the "Y" axis of FIGS. 1 and 7. The left and right outer spheres 26 are clamped onto left and right receptacles 51 in the lower frame member 14 by left and right clamp members 30, which are tightened onto the lower frame member 14 by means of screws 32. When the clamp members 30 are tightened down onto the lower frame member 14, the outer spheres 26 are fixed relative to the lower frame member 14. The left and right clamp members 30 are only loosened when it is necessary to recalibrate the articulator.

The bottom surface of each clamp member 30 and the top surface of each lower receptacle 51 defines an elongated, curved-shaped cavity 53 (See FIGS. 7A and 7B) which cradle the outer sphere 26 and which allow for adjustment of the sphere 26 in all directions. There is a set screw 55 threaded into each clamping member 30 from the side, which sets the end of the cavity 53, beyond which the sphere 26 cannot pass. These set screws 55 are set and fixed in position in the factory and accommodate for manufacturing tolerances in making the cavities 53.

Referring to FIGS. 8–14, the left and right upper receptacles 50, which receive the respective smaller inner spheres 24 of the left and right condyle elements 16, 18, are adjustable in size and include an adjustment or lockout lever 60 which, in one position, permits the inner spheres 24 to shift forward and backward in a slot, and, in a second position, locks the inner spheres 24 against such motion but still permits the upper frame member 12 to pivot about the inner spheres 24. In order to permit this adjustment in size, the receptacles 50 are made up of several parts. First is an elongated cavity 62, having a rear wall 63, a forward wall 65, a bottom wall 67, an upper wall 69, and an inner wall 71. This cavity 62 receives its respective inner sphere 24. While these views show the left cavity 62, it is understood that the right cavity is a mirror image of the left cavity. Riding in a cylindrical opening 73 in the forward wall 65 is a rod 56, which carries at one end a piston head 54. Between the front wall 65 and the piston head 54 and surrounding the rod 56 is a spring 58, which biases the piston head 54 in the rearward direction. The lockout lever 60 is mounted onto the outer surface of the body of the front wall 65 by means of a screw 75, which defines the pivot axis about which the lockout lever 60 pivots. When the lockout lever 60 is in a first, open position, shown in FIGS. 9, 11, and 12, it permits the rod 56 to project out the front surface of the body of the front wall 65, so the piston head 54 can shift forward, permitting the sphere 24 to shift forward relative to the cavity 62. When the lockout lever 60 is in a second, closed position, shown in FIGS. 8, 10, and 13, it stops the piston rod 56 from moving forward and keeps the sphere 24 pressed against the rear wall 63 of the cavity 62, thereby limiting the relative motion between the upper and lower frame members to pivoting motion. It should be noted that an elongated member 77, having a U-shaped cross-section, is fixed to the piston head 54 and encases the piston head 54 and spring 58, to prevent debris from getting into the cavity 62 and interfering with the spring 58. This U-shaped element 77 has an upper T-shaped guide 79, which rides in a slot 81 in the housing 83 which is fixed to the upper frame member 12, and it includes a downwardly-projecting arm 85, which can be used to manually slide the U-shaped element forward. The arm 85 may be used to slide the U-shaped element and its piston head forward in order to insert the inner sphere 24 into its respective cavity 62, for example.

Since each of the condyle elements 16, 18 is a single piece made up of the outer sphere 26, the inner sphere 24, and the connecting shaft 28, if the outer spheres 26 are fixed relative to the lower frame member 14, so are the axial shafts 28 and the inner spheres 24 also fixed relative to the lower frame member 14. However, if the upper frame member 12 is moved backward along the "X" axis, the inner sphere 24 will push against the piston head 54, compressing the spring 58, and the cavity 62 will shift rearwardly relative to the inner spheres 24. (See FIG. 11).

Thus, with the lockout levers in the closed or lockout mode, the articulator behaves like a very simple hinge-type articulator which only allows rotational movement along the "Y" axis. With the lockout levers in the "open" mode, the articulator can more closely and accurately mimic the movements of the human jaw, allowing rotation along the "Y" axis as well as relative motion along the X-Y plane. Of course, each lockout lever is independently operated, so one may be in the "open" position while the other is in the "closed" position.

Figure 3:
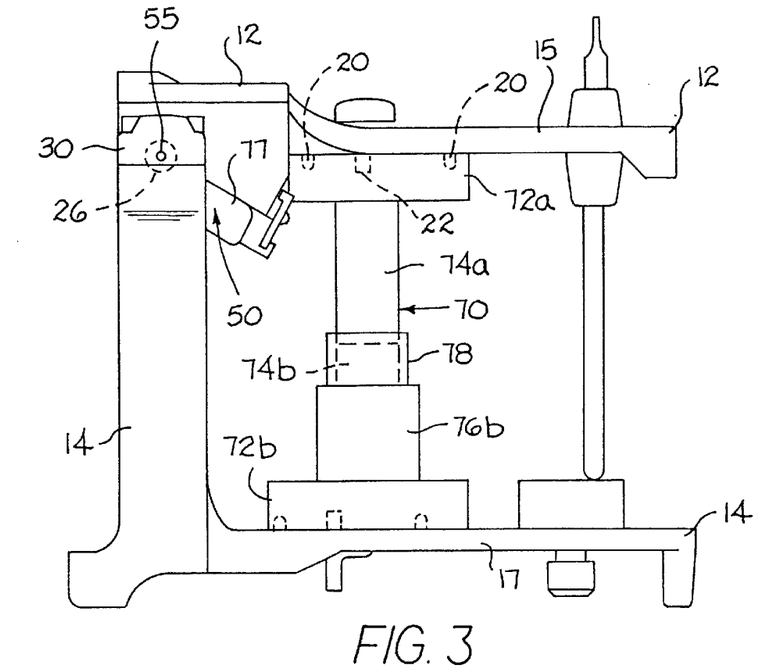
FIG. 3 shows a side view of the articulator of FIG. 1 with a test gauge installed in order to check the alignment of the articulator frame members.
Figure 4:
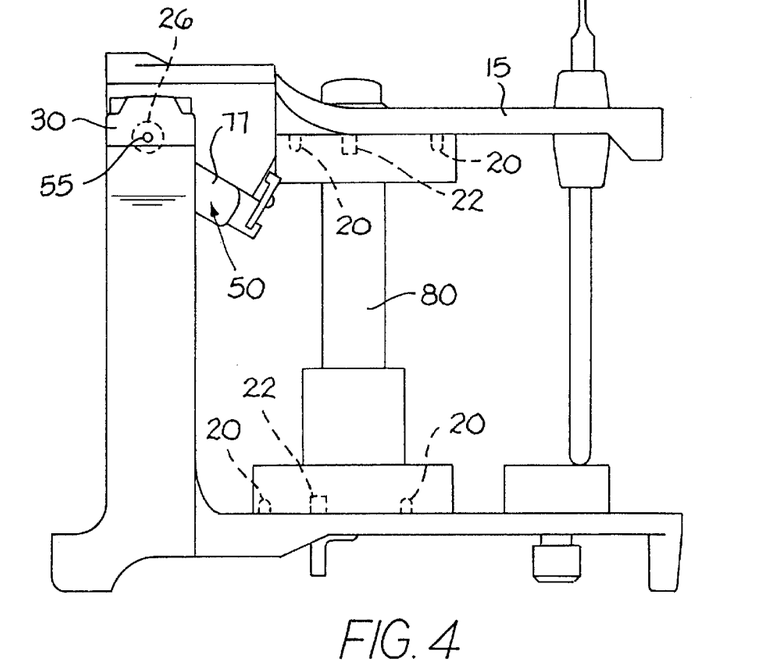
FIG. 4 shows a side view of the articulator of FIG. 1 with a one-piece calibration tool installed in order to bring the articulator frame members into correct alignment.
Figure 4A:
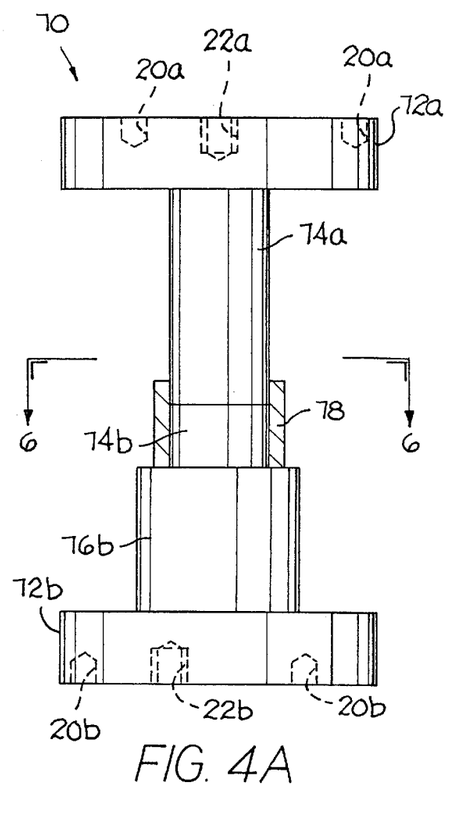
FIG. 4A is a side view, partially in section, of the test gauge of FIG. 3, in a position where the upper and lower frame members are in alignment.
Figure 5:
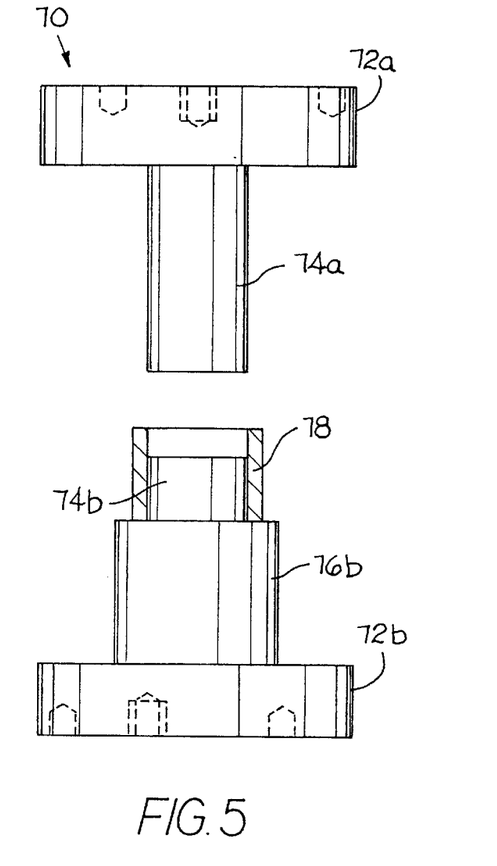
FIG. 5 is a side view, partially in section, of the test gauge of FIG. 3, depicting the separate pieces.
Figure 6:
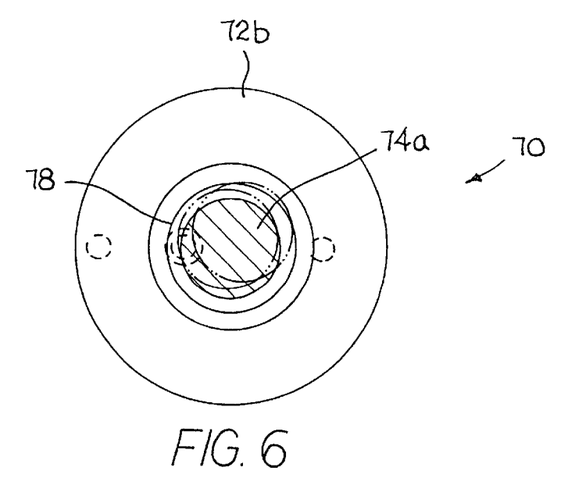
FIG. 6 is a view along line 6—6 of FIG. 4a, showing in phantom a position where the frame members are not in alignment.

The articulator includes a test gauge 70 for checking calibration, also referred to as a split cylinder check tool, as shown in FIGS. 3, 4A and 5, and a calibration tool 80 as shown in FIG. 4.

The test gauge 70 includes three pieces: an upper section, which includes a mounting base 72a and a shaft 74a; a lower section, which includes a mounting base 72b, a shoulder 76b, and a shaft 74b; and a ring or collar 78, the inside diameter of which is just large enough for the collar 78 to slide over the shafts 74a, 74b. Each of the bases, 72a, 72b has first and second recesses 20a, 20b and a central threaded recess 22a, 22b, which receive the respective projections 20 and threaded connector 22 on the respective arm of the articulator.

To check the alignment of the articulator 10, the test gauge 70 is installed in the articulator 10, with the upper and lower mounting bases 72a, 72b mounted on the upper frame member 12 and lower frame member 14, respectively, with recesses 20a, 20b in the mounting bases 72a, 72b receiving the alignment bumps 20, and with the threaded connectors 22 threaded into the threaded recesses 22a, 22b of the mounting bases 72a, 72b, as shown in FIG. 3. The collar 78 is slipped onto the shaft 74a of the upper section of the test gauge 70. Then, the upper frame member 12 is pivoted downwardly until the shaft portions 74a, 74b of the test gauge 70 contact each other, as shown in FIG. 4A. If the shaft portions 74a, 74b meet with flat contact, and if their outer surfaces are aligned, then the collar 78 will slide down the shaft 74a and onto the shaft 74b, coming to rest on the shoulder 76, and the articulator 10 is properly calibrated. If there is any gap between the check pieces, or if their outer surfaces are not aligned such that the collar 78 does not slide onto the shaft 74b and come to rest on the shoulder 76, then the articulator 10 is out of alignment and needs to be recalibrated.

If the articulator 10 is out of calibration as determined by the test gauge 70, the calibration tool 80, shown in FIG. 4, may be used to bring the articulator 10 back into calibration. The calibration tool 80 is practically identical to the test gauge 70 except that it is a single piece and does not have a collar 78.

To calibrate the articulator 10, the screws 32 of the clamp members 30 are loosened, the lockout levers 60 are pivoted into the closed or lockout position, and the calibration tool 80 is mounted on the upper and lower frame members 12, 14, with the alignment bumps 20 and threaded connectors 22 of the upper and lower arms 15, 17 properly received in the top and bottom surfaces of the calibration tool 80, as shown in FIG. 4. This ensures that the upper and lower frame members 12, 14 are properly aligned. Then, with the articulator in proper alignment, the screws 32 are tightened down on the clamp members 30, thereby fixing the outer spheres 26 of the left and right condyle members 16, 18 in the properly aligned position on the lower frame member 14. Once the screws are tightened, the articulator 10 is in proper alignment. The calibrating tool 80 is removed from the articulator 10, and the articulator can again be used.

In an alternative arrangement, instead of clamping the outer spheres 26, they may be glued in position using a chemical-cured or light-cured resin. In this arrangement, the outer spheres 26 preferably have a roughened outer surface. This may be accomplished by casting the spheres in a cast having a rough surface or by sandblasting, and the receptacle 51 should be elongated enough to contain the glue. In that arrangement, there may also be additional screws, perpendicular to the end screw 55, to provide resistance to dislodgement. In this arrangement, the calibration tool 80 is mounted to the upper and lower frames 12, 14, the inner spheres 24 are placed inside the guides of the upper frame 12, and the outer spheres 26 rest in their respective elongated cups 51. The cups 51 are filled with glue and are hardened chemically, or using a curing light. To recalibrate the articulator, the lateral fixating screw is removed, which allows the resin and its outer sphere 26 to be removed from the elongated cup. The resin is then ground away with a dental bur, and the recalibration process described above is used.

Other modifications to the preferred embodiment described above could also be made. For example, the articulator could be turned over, so that the lower and upper frame members are reversed, or the outer spheres could be rotatably mounted while the inner spheres are releasably clamped. Other modifications will also become apparent to those skilled in the art.

What is claimed is:

1. A dental articulator, comprising:
   an upper frame member;
   a lower frame member;
   left and right condyle members mounted on said upper and lower frame members;
   each of said condyle members including an inner spherical portion; an outer spherical portion; and a shaft connecting the inner and outer spherical portions;
   one of said frame members including a first set of left and right receptacles that receive the inner spherical portions of the condyle members, and the other of said frame members including second set of left and right receptacles that receive the outer spherical portions of the condyle members;
   one of said first and second sets of left and right receptacles being releasably secured onto its respective spherical portions of the condyle members so as to be fixed, and the other of said first and second sets of left and right receptacles being pivotably connected to its respective spherical portions of the condyle members, wherein said upper and lower frame members pivot relative to each other about said pivotably connected spherical portions to simulate the action of a human jaw.

2. A dental articulator as recited in claim 1, wherein said upper frame member includes the first set of left and right receptacles and the lower frame member includes the second set of left and right receptacles.

3. A dental articulator as recited in claim 1, wherein the second set of left and right receptacles is releasably clamped onto the outer spherical portions of the condyle members, and the first set of left and right receptacles is pivotably mounted onto the inner spherical portions of the condyle members.

4. A dental articulator as recited in claim 1, wherein the set of left and right receptacles that is releasably secured to its respective spherical portions receives left and right end screws which define the outermost positions the respective spherical portions may take in said set of releasably secured receptacles.

5. A dental articulator as recited in claim 1, and further comprising left and right clamping members received by said set of receptacles that is releasably secured onto its respective spherical members so as to releasably secure the spherical members by clamping.

6. A dental articulator, comprising:
   an upper frame member;
   a lower frame member;
   left and right condyle members mounted on said upper and lower frame members;
   each of said condyle members including an inner spherical portion; an outer spherical portion; and a shaft connecting the inner and outer spherical portions;
   said upper frame member including a first set of left and right receptacles, which pivotably receive the inner spherical portions of the condyle members;
   said lower frame member including a second set of left and right receptacles and a set of left and right clamping members, wherein said clamping members releasably lock the outer spherical portions of the condyle members in said second set of left and right receptacles, so that said upper frame member pivots about said lower frame member by pivoting about said inner spherical portions.

7. A dental articulator as recited in claim 1, wherein the set of left and right receptacles that is pivotably connected to its respective spherical portions defines left and right elongated receptacle chambers; left and right spring-loaded pistons in the respective elongated receptacle chambers; and piston rods fixed to said pistons, wherein the elongated receptacle chambers have forward walls defining openings through which the piston rods extend; and further comprising movable closures which selectively open and close said forward openings so that, when said closures are closed, said pistons are fixed in their respective elongated receptacle chambers, and, when said closures are open, said pistons may move axially in their respective elongated chambers.

8. A dental articulator as recited in claim 6, wherein said left and right upper receptacles include left and right elongated receptacle chambers; left and right spring-loaded pistons in the respective elongated receptacle chambers; and piston rods fixed to said pistons, wherein the elongated receptacle chambers have forward walls defining openings through which the piston rods extend; and further comprising movable closures which selectively open and close said forward openings so that, when said closures are closed, said pistons are fixed in their respective elongated receptacle chambers, and, when said closures are open, said pistons may move axially in their respective elongated chambers.

9. A dental articulator as recited in claim 1, wherein each of said upper and lower frame members comprises a forwardly-projecting arm; and each of said arms includes alignment projections and a threaded fastener for securing a dental casting to said arm.

10. A dental articulator as recited in claim 9, and further comprising a check gauge having upper and lower base portions, which receive the alignment projections and threaded fasteners of said forwardly-projecting arms; upper and lower shaft portions, which are in alignment with each other when the articulator is properly calibrated; and a sleeve which fits over the upper and lower shaft portions with a close tolerance and slides smoothly up and down said upper and lower shaft portions when the articulator is properly calibrated.

11. A method of calibrating a dental articulator having an upper frame member and a lower frame member, comprising the steps of:

providing left and right dumbbell-shaped condyle elements between the upper and lower frame members, each condyle element including an outer spherical portion and an inner spherical portion connected by a shaft;

mounting the inner spherical portions on one of the frame members;

mounting the outer spherical portions on the other frame member;

with one set of the spherical portions mounted loosely on its respective frame member and the other set pivotably mounted on its respective member, mounting an alignment fixture on the upper and lower frame members to put the frame members into proper alignment; and then fixing the loosely mounted spherical portions in the properly-aligned position.

12. A method as recited in claim 11, wherein the loosely mounted spherical portions are fixed by clamping.

13. A method as recited in claim 11, wherein the loosely mounted spherical portions are fixed by gluing.

* * * * *

UNITED STATES PATENT AND TRADEMARK OFFICE
CERTIFICATE OF CORRECTION

Page 1 of 1

PATENT NO. : 6,299,442 B1
DATED : October 9, 2001
INVENTOR(S) : John Shiao, Jesse Chen and Allen Steinbock It is certified that error appears in the above-identified patent and that said Letters Patent is hereby corrected as shown below:

<u>Column 1,</u>
Line 18, delete "amounts" and insert therefor -- mounts --.

Signed and Sealed this

Nineteenth Day of March, 2002

*Attest:*

JAMES E. ROGAN
*Director of the United States Patent and Trademark Office*

*Attesting Officer*